US010338203B2

(12) United States Patent
Fan et al.

(10) Patent No.: US 10,338,203 B2
(45) Date of Patent: Jul. 2, 2019

(54) CLASSIFICATION PREPROCESSING IN MEDICAL ULTRASOUND SHEAR WAVE IMAGING

(75) Inventors: Liexiang Fan, Sammamish, WA (US); Paul Freiburger, Seattle, WA (US); John Benson, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1033 days.

(21) Appl. No.: 13/229,408

(22) Filed: Sep. 9, 2011

(65) Prior Publication Data

US 2013/0066204 A1    Mar. 14, 2013

(51) Int. Cl.
 G01S 7/52    (2006.01)
 A61B 8/08    (2006.01)
 A61B 8/14    (2006.01)
 G03B 42/06   (2006.01)

(52) U.S. Cl.
 CPC ........ *G01S 7/52036* (2013.01); *A61B 8/0858* (2013.01); *A61B 8/485* (2013.01); *A61B 8/5207* (2013.01); *A61B 8/5223* (2013.01); *A61B 8/14* (2013.01); *G01S 7/52022* (2013.01); *G03B 42/06* (2013.01)

(58) Field of Classification Search
 CPC .... A61B 8/08; A61B 8/485; A61B 2019/5276
 USPC ....................... 600/407, 437, 438
 See application file for complete search history.

(56) References Cited

U.S. PATENT DOCUMENTS

| | | | | |
|---|---|---|---|---|
| 5,487,387 | A * | 1/1996 | Trahey et al. | 600/438 |
| 5,840,038 | A * | 11/1998 | Xue et al. | 600/512 |
| 6,176,827 | B1 * | 1/2001 | Cohen-Bacrie | A61B 8/0825 600/438 |
| 8,187,187 | B2 | 5/2012 | Fan et al. | |
| 8,494,791 | B2 * | 7/2013 | Hazard et al. | 702/56 |
| 2003/0018442 | A1 * | 1/2003 | Yamaguchi | G06F 17/15 702/69 |
| 2005/0252295 | A1 * | 11/2005 | Fink et al. | 73/603 |
| 2007/0049824 | A1 * | 3/2007 | Konofagou et al. | 600/437 |
| 2008/0131511 | A1 | 6/2008 | Okada et al. | |
| 2008/0242997 | A1 * | 10/2008 | Lynch | G01N 29/07 600/455 |
| 2008/0249408 | A1 * | 10/2008 | Palmeri et al. | 600/438 |
| 2009/0192722 | A1 * | 7/2009 | Shariati et al. | 702/19 |
| 2010/0063393 | A1 * | 3/2010 | Moradi et al. | 600/442 |
| 2010/0168566 | A1 | 7/2010 | Bercoff et al. | |
| 2010/0241001 | A1 | 9/2010 | Dahl et al. | |

(Continued)

OTHER PUBLICATIONS

Nightingale et al. (Ultrasound in Med. And Biol. vol. 21, No. 6, pp. 745-751, 1995).*

(Continued)

*Primary Examiner* — Jennifer Dieterle (57) ABSTRACT

Classification preprocessing is provided for medical ultrasound shear wave imaging. In response to stress, the displacement at one or more locations in a patient is measured. The displacement over time is a curve representing a shift in location. One or more characteristics of the curve, such as signal-to-noise ratio and maximum displacement, are used to classify the location. The location is classified as fluid or fluid tissue, solid tissue, or non-determinative. Subsequent shear imaging may provide shear information for locations of solid tissue and not at other locations.

22 Claims, 3 Drawing Sheets

(56) References Cited

U.S. PATENT DOCUMENTS

| | | | |
|---|---|---|---|
| 2010/0262009 A1* | 10/2010 | Lynch | G01S 7/52036 600/455 |
| 2010/0280341 A1* | 11/2010 | Boock et al. | 600/309 |
| 2010/0286516 A1 | 11/2010 | Fan et al. | |
| 2010/0286520 A1* | 11/2010 | Hazard et al. | 600/439 |
| 2011/0245678 A1* | 10/2011 | Tamura | A61B 8/08 600/453 |
| 2011/0251529 A1* | 10/2011 | Petruzzello | A61B 8/08 601/3 |
| 2012/0108968 A1* | 5/2012 | Freiburger | A61B 8/0825 600/443 |
| 2012/0244564 A1* | 9/2012 | Walker et al. | 435/13 |
| 2013/0102932 A1* | 4/2013 | Cain | A61N 7/00 601/2 |
| 2013/0131511 A1 | 5/2013 | Petersen et al. | |

OTHER PUBLICATIONS

Rebecca C. Boll, et al., *Characterization of Cysts using Differential Correlation Coefficient Values from 2D Breast Elastography: Preliminary Study*, National Institute of Health, Ultrasound Med Biol., p. 1-19, Jan. 2008.

\* cited by examiner

Echo image shows the solid and fluid tissue (colorbar shows log compression scale)

Signal to noise ratio derived from displacement profile shows clearly the solid and fluid tissue

CLASSIFICATION PREPROCESSING IN MEDICAL ULTRASOUND SHEAR WAVE IMAGING

BACKGROUND

The present embodiments relate to ultrasound imaging. In particular, ultrasound shear wave imaging may be improved.

Shear wave velocity information may be useful for diagnosis. Shear wave information may indicate tissue characteristics in addition to acoustic impedance (e.g., B-mode) and Doppler (e.g., flow mode) imaging. However, the complexity of shear wave propagation in tissue may result in significant errors. For example, shear wave velocity may be less accurately determined for fluid or fluid tissue, resulting in seemingly arbitrary values.

To remove the effects of fluid from shear wave images, fluid regions may be separated from solid tissue regions by measuring the flow after stirring. For stirring, acoustic energy is used to generate streaming in fluid. A correlation coefficient between successive or sequential echo signals is computed to distinguish solid tissue from the stirred fluid. However, in live scanning, the motion of solid tissue may produce the same magnitude of decorrelation as fluid motion induced by the acoustic energy stirring. The ability to distinguish may be limited.

BRIEF SUMMARY

By way of introduction, the preferred embodiments described below include methods, instructions, and systems for classification preprocessing for medical ultrasound shear wave imaging. In response to stress, the displacement at one or more locations in a patient is measured. The displacement over time is a curve representing shift in the position of the location. One or more characteristics of the curve, such as signal-to-noise ratio and maximum displacement, are used to classify the location. The location is classified as fluid or fluid tissue, solid tissue, non-determinative, or other class. Subsequent shear imaging may provide shear information for locations of solid tissue and not at other locations.

In a first aspect, a method is provided for classification preprocessing to be used in medical ultrasound shear wave imaging. Displacement over time at a first location within a patient in response to an impulse excitation is measured with ultrasound. A maximum of the displacement over time is determined. A signal-to-noise ratio of the displacement over time is determined. A processor classifies the first location as a first one of a plurality types of tissue. The classification is a function of the maximum of the displacement over time and the signal-to-noise ratio of the displacement over time.

In a second aspect, a non-transitory computer readable storage medium has stored therein data representing instructions executable by a programmed processor for classification preprocessing in medical ultrasound shear wave imaging. The storage medium includes instructions for determining a displacement profile of response in a patient, calculating a first characteristic of the displacement profile, distinguishing fluid and fluid tissue from solid tissue based, at least in part, on the first characteristic, masking out shear wave information from an image for fluid or fluid tissue.

In a third aspect, a system is provided for classification preprocessing in medical ultrasound shear wave imaging. A transducer is configured to transmit an acoustic impulse excitation into a patient and configured to scan with ultrasound a region of the patient. A receive beamformer is configured to generate data representing the region at different times after the acoustic impulse excitation. The data is generated from the scan with ultrasound. A processor is configured to estimate tissue displacement induced by the acoustic impulse excitation, derive at least one parameter describing a characteristic of a profile of the tissue displacement, and classify tissue in the region based on at least the one parameter. A display is configured to display an image representing shear for first locations. The first locations are determined as a function of the classification of the tissue.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Locations in a region of interest are classified as solid tissue or other types of material. Solid tissue regions may allow for more accurate measurement of shear. Other types, such as fluid or fluid tissue, may be less accurately measured for shear velocity. Locations associated with solid tissue are included in shear imaging, and other locations may be pre-excluded from imaging of the shear wave propagation field. Classification may alternatively or additionally identify regions associated with shadowing or/and hypo echoic regions for exclusion from shear wave imaging.

A region of interest may include fluid (e.g., blood or urine), bone, and tissue. Tissue may include fluid like tissue (i.e., fluid tissue) or solid tissue. Solid tissues include muscle, fat, organs or other structure with a relatively more elastic character than fluid and bone. Cysts or other tissue structure may have a high fluid content. To reduce inaccuracies in shear wave imaging, the fluid tissue or fluid is segmented from solid tissue.

When solid tissue and fluid tissue are excited by an impulse force, both tissues are displaced. The characteristic of the displacement profile over time may be different by the type of tissue. Displacement in solid tissue is governed by the shear wave equation, and displacement in fluid tissue is governed by Navier-Stokes equation. The resulting displacement profile in fluid tissue shows significant noise compared with the displacement profile in solid tissue. The signal-to-noise ratio (SNR) of echo signal also contributes to the SNR of the displacement profile.

Other parameters of the displacement profile in addition to or as an alternative to the SNR may be used for classifying. For example, the maximum displacement in the displacement profile may differentiate fluid or fluid tissue from a hypo echoic region of solid tissue. Used together, the SNR and maximum displacement may discriminate fluid and fluid tissue from soft and hard solid tissue.

Tissue displacements induced by impulse excitation are estimated. At least one parameter describing the characteristics of the displacement profile is estimated. Tissues are classified into at least one category from a plurality of categories based on the derived parameter. In one example, the SNR and the maximum value of the displacement profile are used to classify tissue into fluid or solid tissue types. In another example, another characteristic, such as a statistic (e.g., mean or higher order statistic) of an echo signal is used with the SNR and maximum displacement to classify.

Figure 1:
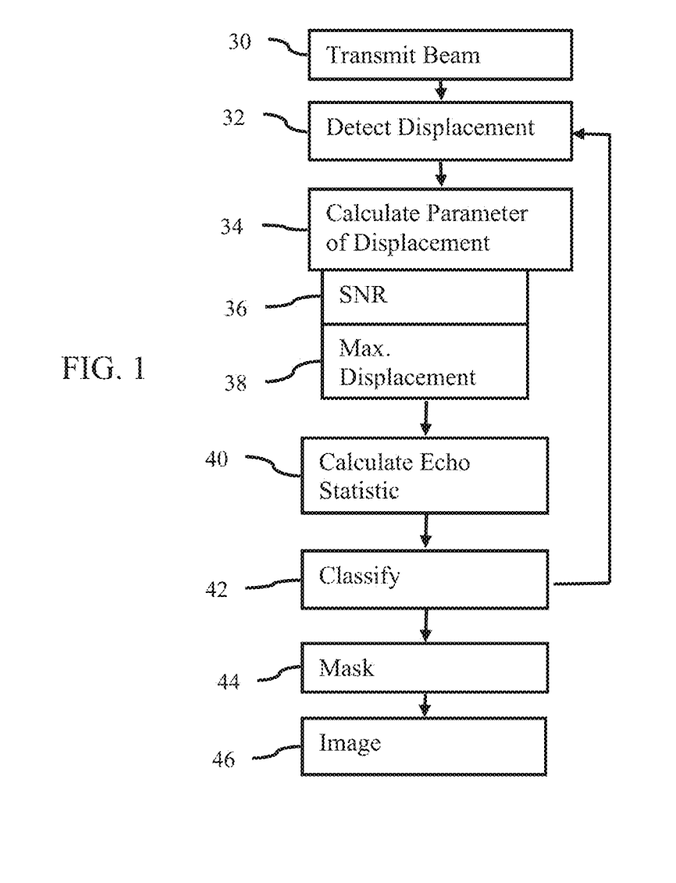
FIG. 1 is a flow chart diagram of one embodiment of a method for classification preprocessing to be used in medical ultrasound shear wave imaging.

FIG. 1 shows a method for classification preprocessing to be used in medical ultrasound shear wave imaging. The method is implemented by the system of FIG. 7 or a different system. Additional, different, or fewer acts may be provided. For example, act 30 is not performed and the source of stress is provided by the body, manually, using a thumper, or by other mechanism. As another example, different parameters of the displacement are calculated instead of SNR in act 36 and/or maximum displacement in act 38. Act 40 is optional. In yet another example, acts 44 and/or 46 are not provided, and the classification is used for other purposes. The acts are performed in the order described or shown, but may be performed in other orders.

Figure 2:
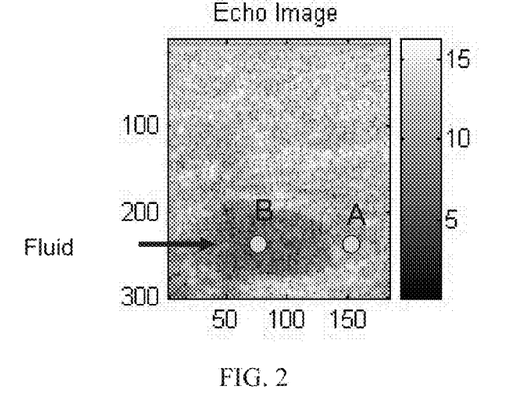
FIG. 2 is an example ultrasound medical image.

The description of the method of FIG. 1 is provided in the context of an example represented in FIG. 2. FIG. 2 shows a B-mode or echo image of a two dimensional region of breast tissue. The method may be used for other organs. The region includes a cyst (darker region around the location B). More than one or no cysts may be in the region. The region may include other types of material, such as bone or fluid. Two representative locations A and B are shown. Location A is within a solid tissue area, and location B is inside fluid tissue. The method is performed for one or more locations. In one embodiment, the method is performed for each of the B-mode or scan sample locations in an entire field of view or a region of interest. Less or more dense sampling may be used.

In act 30 of FIG. 1, an acoustic excitation is transmitted into a patient. The acoustic excitation acts as an impulse excitation. For example, a 400 cycle transmit waveform with power or peak amplitude levels similar or higher than B-mode transmissions for imaging tissue is transmitted. In one embodiment, the transmission is a radiation force sequence applied to the field of view. Any acoustic radiation force imaging (ARFI) sequence may be used.

The transmission is configured by power, amplitude, timing or other characteristic to cause stress on tissue sufficient to displace the tissue at one or more locations. For example, a transmit focus is positioned near a bottom, center of the field of view to cause displacement throughout the field of view. The transmission may be repeated for different sub-regions.

The excitation is transmitted from an ultrasound transducer. The excitation is acoustic energy. The acoustic energy is focused, resulting in a three-dimensional beam profile. The excitation is focused using a phased array and/or mechanical focus. The excitation may be unfocused in one dimension, such as the elevation dimension. The excitation is transmitted into tissue of a patient.

In act 32, a displacement profile of response in the patient is determined. For example, the displacement profiles for locations A and B are demonstrated in FIG. 3. The excitation causes displacement of the tissue. A shear wave is generated and propagates from the focal region. As the shear wave travels through tissue, the tissue is displaced. Longitudinal waves or other causes of displacement may be used. The tissue is forced to move in the patient.

Figure 3:
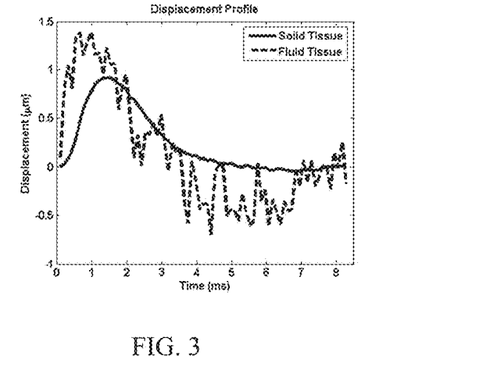
FIG. 3 is an example graph of displacement over time of two locations represented in FIG. 2.

The displacement caused by the force or stress is measured. The displacement is measured over time at one or more locations. The displacement measurement may begin before the stress or impulse ends, such as using a different frequency or coding. Alternatively, the displacement measurement begins after the impulse ends. Since the shear, longitudinal or other wave causing the displacement in tissue spaced from the point or region of stress takes time to travel, the displacement from a relaxed or partially stressed state to a maximum displacement and then to a relaxed state may be measured, as represented in FIG. 3. Alternatively, the displacement is measured only while the tissue is relaxing to form the maximum.

The measurement is of the amount or magnitude of the displacement. The tissue is moved in any direction. The measurement may be along the direction of greatest movement. The magnitude of the motion vector is determined. Alternatively, the measurement is along a given direction, such as perpendicular to the scan line regardless of whether the tissue is displaced more or less in other directions.

The displacement is detected with ultrasound scanning. A region, such as a region of interest, entire field of view, or sub-region of interest, is scanned with ultrasound. For a given time, ultrasound is transmitted to the tissue or region of interest. Any now known or later developed displacement imaging may be used. For example, pulses with 1-5 cycle durations are used with an intensity of less than 720 $mW/cm^2$. Pulses with other intensities may be used.

Echoes or reflections from the transmission are received. The echoes are beamformed, and the beamformed data represents one or more locations. To detect the displacement, ultrasound energy is transmitted to the tissue undergoing displacement and reflections of the energy are received. Any transmission and reception sequence may be used.

By performing the transmitting and receiving multiple times, data representing a one, two, or three-dimensional region at different times is received. The transmission and reception are performed multiple times to determine change due to displacement. By repetitively scanning with ultrasound, the position of tissue at different times is determined.

The echoes are detected using B-mode or Doppler detection. The displacement is detected from the differences for each spatial location. For example, the velocity, variance, shift in intensity pattern (e.g., speckle tracking), or other information is detected from the received data as the displacement.

In one embodiment using B-mode data, the data from different scans is correlated. For example, a current set of data is correlated multiple times with a reference set of data. Different relative translations and/or rotations between the two data sets are performed. The location of a sub-set of data centered at a given location in the reference set is identified in the current set.

The reference is a first set of data or data from another scan. The same reference is used for the entire displacement detection or the reference data changes in an ongoing or moving window.

The correlation is one, two or three-dimensional. For example, correlation along a scan line away and toward the transducer is used. For a two dimensional scan, the translation is along two axes with or without rotation. For three dimensional scanning, the translation is along three axes with or without rotation about three or fewer axes. The level of similarity or correlation of the data at each of the different offset positions is calculated. The translation and/or rotation with a greatest correlation represents the motion vector or offset for the time associated with the current data being compared to the reference.

Any now known or later developed correlation may be used, such as cross-correlation, pattern matching, or minimum sum of absolute differences. Tissue structure and/or speckle are correlated. Using Doppler detection, a clutter filter passes information associated with moving tissue. The velocity of the tissue is derived from multiple echoes. The velocity is used to determine the displacement towards or away from the transducer. Alternatively, the relative or difference between velocities at different locations may indicate strain or displacement.

FIG. 3 shows two example displacement profiles. The magnitude in distance of the motion vector over time from reference data is shown. The period of analysis is over about 10 milliseconds, but may be longer or shorter. The displacement profile for the location A associated with solid tissue has a smoother appearance than the displacement profile for the location B associated with the fluid tissue. Other displacement profiles are possible.

In act 34, a characteristic of the displacement profile is calculated. Any characteristic may be used. More than one characteristic may be calculated. In the example of FIG. 1, both the SNR of the displacement profile (act 36) and the maximum displacement (act 38) are calculated. Different, additional, or fewer characteristics may be calculated.

In act 36, the SNR of the displacement profile is determined. The SNR of the displacement over or as a function of time is determined by identifying noise from the profile. Noise may be identified in any way, such as selecting high frequency components of the profile. A Fourier transform may be used to determine the high frequency noise.

In one embodiment for identifying the noise, the displacement profile is filtered. A low pass filter, such as a Butterworth filter, is applied to the profile (i.e., temporal filtering). The filter is an infinite impulse response (IIR) filter or a finite impulse response (FIR) filter. The filtered displacement over time is subtracted from the displacement over time prior to filtering. The difference represents the noise.

Figure 4:
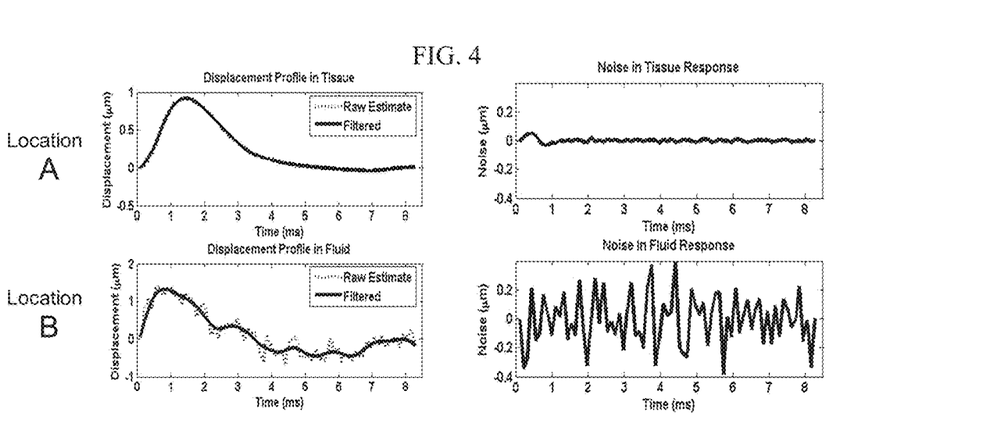
FIG. 4 shows example smoothed and noise displacement curves for the two locations represented in FIG. 2.

FIG. 4 shows the displacement profiles for locations A and B before and after filtering (left side). The unfiltered displacement curves are also represented in FIG. 4 as the dashed lines on the left side. In the filtered displacement profile, the high frequency information is removed or reduced. The noise obtained by subtracting the filtered displacement curves from the unfiltered displacement curves is also shown (right side). The noise is more variable and of greater amplitude for location B, associated with fluid tissue, then for location A, associated with solid tissue.

To calculate the SNR, the noise information is quantified. The root mean square (RMS) of the noise signal is calculated to represent the noise level. Other calculations may be used, such as an average of the absolute values of the peaks.

To determine the SNR, the signal level is calculated. In one embodiment, the signal level is represented by the area under the filtered displacement profile. The integral of the filtered displacement is calculated. Other signal level measurements may be used.

The SNR is provided by dividing the signal (e.g., integral of the filtered displacement) by the noise (e.g., RMS of the noise). Other functions may be used, including other variables. In the example from FIG. 4, the SNR is calculated for two locations A, B. The SNR may be calculated for other locations.

In act 38, the maximum displacement is calculated. The maximum displacement is calculated from the displacement profile. The peak or highest amount of motion or magnitude of shift by the tissue along a line, within a plane, or within a volume is calculated. The smoothed or filtered displacement curve is used for the maximum calculation. In other embodiments, the raw or unfiltered displacement curve may be used. The maximum value over the entire or portion of the profile is identified or determined. In the example of FIG. 4, the maximum displacement of 0.9 micrometers occurs at about 1.7 milliseconds for location A, and the maximum displacement of 1.3 micrometers occurs at about 0.8 milliseconds for location B.

In optional act 40, another parameter other than from the displacement profile is calculated. In the example of FIG. 1, other parameters may include a statistic of the echo information, echo signal's signal to noise ratio, and/or de-correlation measurement of echo signal over time. For example, the mean of the B-mode information for a location over the same period used for the displacement profile is calculated. Higher order statistics may be calculated instead or in addition. Any statistic or other parameter may be used for classification. The statistic may be spatial and/or temporal. Echo signal's SNR may be calculated as ratio between the receive signal intensity with and without transmits. De-correlation coefficient may be calculated as the 1 minus the normalized correlation coefficient of the echo signals detected before and post the ARFI or other excitation beam.

In act 42, one or more locations are classified. The tissue or other material at each location is independently or separately classified. The classification for each location relies on data for that location and not data for other locations. In alternative embodiments, spatial filtering or information from adjacent locations may be used for classifying a given location.

The classification identifies the material. Any type of material may be identified. In one embodiment, the classification identifies the location as fluid (a category or type including fluid tissue), solid tissue, or other (e.g., not determinable). The location is classified as one of the group. The group may include more or fewer options or classes, such as selecting between (a) fluid or fluid tissue and (b) solid tissue.

The classifying distinguishes solid tissue from other materials, such as from fluid tissue and another class. A processor performs the classifying without user selection or input. The processor users the characteristic of the displacement profile with or without other information or parameters. For example, the processor classifies as a function of the SNR, maximum displacement, or SNR and maximum displacement. Classifying with the SNR and the maximum displacement may distinguish between fluid tissue, solid tissue and other or non-determined.

Figure 5:
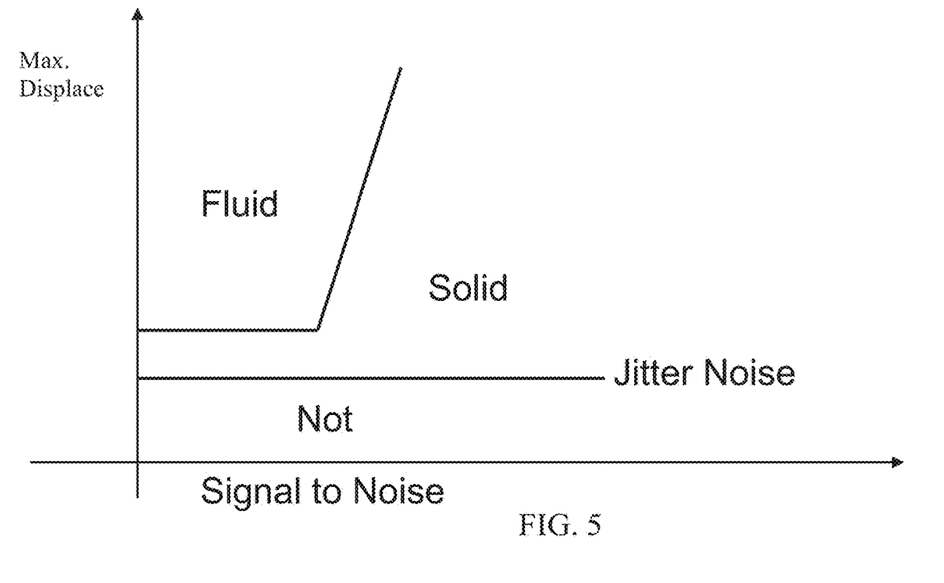
FIG. 5 is a graphical representation of classification based on maximum displacement and signal-to-noise ratio, according to one embodiment.

FIG. 5 shows one embodiment of classification using two parameters, SNR and maximum displacement, of the displacement profile. The jitter noise level is used to class a "not determined" category. If the maximum displacement is low, there may be insufficient information or non-tissue or fluid material. For low maximum displacement, there is no classification or the class is the "not determined" category. For lower SNR and higher displacement, the material at the location is classified as fluid or fluid tissue. For other combinations of the two parameters, the material at the location is classified as solid tissue. Other functions than shown in FIG. 5 may be used.

The classification function is based on experiments, a mathematical function, statistics, or other information. For example, fuzzy logic is used to classify. In this method, a membership function of each tissue type is empirically defined for each parameter (e.g. SNR, maximum displacement), the outputs of each membership function given the input parameters at a location are summed to generate the likelihood of a tissue type. The maximum value of the sum corresponds to the tissue type to be assigned. As another example, machine learning from a collection of training samples or data with known ground truth regarding the class is used to determine statistics or a matrix function for classifying. A probability function indicates the likelihood of each class for a given location, and the class with the highest probability is selected. The classification is performed using a lookup table, fuzzy logic function, programmed function, or matrix function.

Referring again to FIG. 1, the feedback from act 42 to act 32 represents repeating the classifying for a plurality of locations. For example, the displacement profile and characteristics for the displacement profile are determined for each location in a field of view. The repetition uses the same or different transmission in act 30. Where the region of interest is sufficiently small, one impulse is used. The displacement at different locations is determined using a window centered on each of the locations. For each location, the window or kernel is centered over the location. The data representing spatial locations within the window is used for correlation. Displacement is separately determined for each location. In other embodiments, the transmission act 30 is repeated. Displacements for one, some or a subset of a region of interest are determined in response to each transmission of act 30.

The displacement profiles are detected over any size region. In one embodiment, the displacement is detected in a region of interest likely to include the tissue to be diagnosed, such as about ⅓ to ½ the complete scan region for B-mode imaging. Greater, lesser, or no region of interest may be used, such as detecting displacement over the entire imaging region. Narrower regions of interest may allow for displacement detection with fewer repetitions of transmitting the excitation waveform of act 30. Depending on the number of receive beams that may be formed and the sample density, none, one, or more repetitions may be used.

Figure 6:
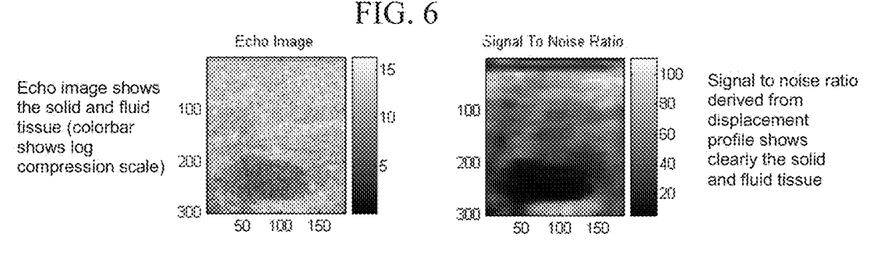
FIG. 6 shows two example medical images with a B-mode image on the left and an image generated from signal-to-noise ratio on the right.

Full sampling, such as sampling displacement on every B-mode sample location, may be used. Greater or lesser (e.g., sparse) sampling of displacement relative to the B-mode scan grid may be used. FIG. 6 shows a B-mode image and an SNR image for the same sampling density. The SNR information better indicates the cyst. The SNR image may or may not be displayed to the user.

The classification is used to spatially mask out shear wave information in act 44. Shear wave information is to be displayed for locations of solid tissue. For other locations, such as for fluid tissue or non-determined locations, the shear wave information is not displayed. The locations are masked. Based on the masking, determined shear wave information is not displayed, or shear wave information is not even calculated. The unreliable shear information from fluid or fluid tissue is not presented to the user in the image, avoiding confusion.

In act 46, shear wave imaging is performed. The shear velocity, modulus or other information determined from tissue reaction to a shear wave is detected. Any shear imaging may be used. Due to the masking of act 44, the displayed image represents shear wave information for solid tissue regions and not for fluid or fluid tissue regions.

The shear information is detected for the same locations as the displacement. Different transmission and scanning are used for shear imaging than displacement calculation. Alternatively, the same transmissions and even displacement profiles are used for the shear imaging as for classifying. The time for the shear wave to travel from the origin (e.g., transmit focal region) to the location is determined. The maximum displacement or other part of the displacement profile indicates the time of arrival of the shear wave. The velocity of the shear wave is calculated from the timing information.

For shear wave imaging, an impulse excitation generates a shear wave at a spatial location. Where the excitation is sufficiently strong, a shear wave is generated. The shear wave propagates through tissue more slowly than the longitudinal wave along the acoustic wave emission direction. The shear wave propagates various directions, including a direction perpendicular to the direction of the applied stress. The displacement of the shear waves is greater at locations closer to the location at which the shear wave is generated.

Ultrasound data is obtained. At least some of the ultrasound data is responsive to a shear wave. A region of interest is monitored to detect the shear wave. The region of interest is any size, such as 6 mm in lateral and 10 mm in axial. This detection region is monitored by ultrasound. For example, B-mode scans are performed to detect tissue displacement caused by the shear wave. Doppler, color flow, or other ultrasound mode may be used to monitor for the shear wave.

The monitoring is performed for any number of scan lines. For example, four receive beams are formed in response to each transmission. After transmitting the excitation to generate the shear wave, B-mode transmissions are performed repetitively along a single scan line and receptions along four adjacent scan lines. In other embodiments, only a single receive beam or other numbers of receive beams are formed in response to each transmission. Any number of repetitions may be used, such as about 120 times. Some of the ultrasound data, such as at the beginning or end of the repetitions, may not be responsive to the shear wave.

As the shear wave propagates through the scan lines, the B-mode intensity may vary due to displacement of the tissue. For the monitored scan lines, a sequence of data is provided representing a time profile of tissue motion resulting from the shear wave. For example, data from a plurality of spatial locations (e.g., along the scan lines) is correlated as a function of time. Any elasticity detection may be used. For each depth or spatial location, a correlation over a plurality of depths or spatial locations (e.g., kernel of 64 depths with the center depth being the point for which the profile is calculated) is performed. Two or three-dimensional displacement in space may be used. One-dimensional displacement along a direction different than the scan lines or beams may be used.

The spatial offset with the highest or sufficient correlation at a given time indicates the amount of displacement. Displacements are determined for a given location at different times. The temporal profile for a given location indicates detection of the shear wave. The profile is examined for a non-noise or single instance of variation. A peak in the profile, with or without temporal low pass filtering, indicates the passing of the shear wave front. The greatest displacement is selected, but the average or other displacement statistic may be used. The maximum shear at a given location is detected. Alternatively, an average or other shear is detected.

To monitor a larger region, additional receive beams are formed in response to the monitoring transmit beam. Alternatively, another shear wave is generated and the transmit beams and receive beams are provided at a different distance from the shear wave generation point. In the 6 mm×10 mm example above, 36 receive scan lines may be provided. At four receive beams per transmit beam, the process is repeated for different lateral spacing nine times. For each receive beam location, a time profile of motion information is provided, represented by the ultrasound data. Transmissions along different scan lines to monitor a same shear wave are avoided during formation of the temporal profile to provide higher temporal resolution, but interleaved or shifting scanning positions may be provided.

The discussion above is for one depth. The sampling may be arranged to provide one gate covering the entire axial extent of the region of interest. In another embodiment, samples are obtained at multiple depths for each receive beam. A separate time profile is provided for each axial depth as well as lateral location. Any number of depths may be used, such as about 200 for 5 mm or 400 for 10 mm.

Ultrasound data representing different locations in the region of interest is obtained. The ultrasound data is obtained in real-time with the scanning or obtained from a memory. For each location, the motion information represents the response at different times. Other scanning, monitoring, or techniques may be used to obtain ultrasound data to estimate shear magnitude.

Shear velocity is detected for the different spatial locations of the tissue. For each location, the displacement as a function of time is determined. The shear velocity is obtained by determining a time from generation of the shear wave until detection of the shear wave at a different location. The time and distance to the location determine the velocity. The distance is known from the scan line spacing (i.e., the transmit beam position for generating the shear wave and the receive beam position for detecting the shear wave). The time is known from the relative time between generation and detection of the shear wave.

Other techniques may be used to detect the peak in the profile. For example, a regression is applied. Since the shear wave velocity is linear, a robust linear regression with automated outlier detection may indicate the shear wave velocity. The ultrasound data for all of the sample points in the region of interest is plotted for distance as a function of time or by time and distance. The linear regression is applied to the plot or data, providing a line fit to the data. The slope of the line indicates the shear wave velocity.

The shear wave information is used for a color overlay or other modulation of display values. For example, shear wave information is displayed over or with B-mode information. The displacement data is in a display format or may be scan converted into a display format. The displacement data is color or gray scale data, but may be data prior to mapping with gray scale or color scale. The information may be mapped linearly or non-linearly to the display values.

The image represents the displacement information, such as shear or moduli (e.g., the shear moduli) for the different locations. Where the values are determined for all of the grid points in a region of interest or field of view, the pixels of the display represent the shear velocities for that region. The display grid may be different from the scan grid and/or grid for which displacements are calculated. Color, brightness, luminance, hue, or other characteristic is modulated as a function of the displacement.

The image may include other data. For example, B-mode or other data representing tissue, fluid, or contrast agents in the same region is included. The displacement data is used for an overlay of or combination with the other data. The other data assists the user in determining the location of the beam relative to the tissue to be treated.

Figure 7:
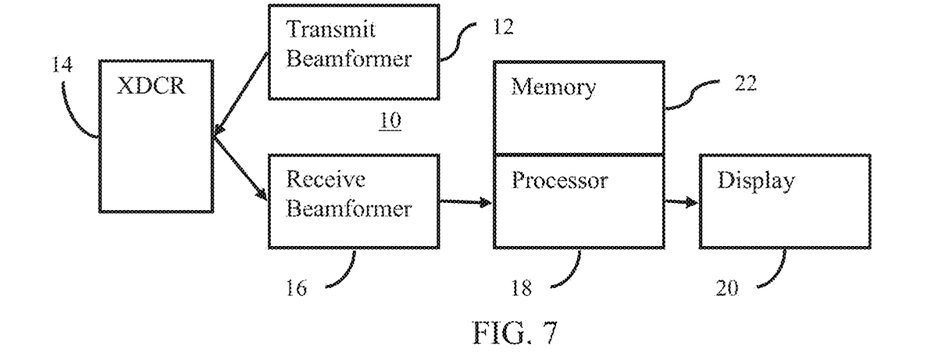
FIG. 7 is a block diagram of one embodiment of a system for classification preprocessing in medical ultrasound shear wave imaging.

FIG. 7 shows one embodiment of a system 10 for classification preprocessing in medical ultrasound shear wave imaging. The system 10 implements the method of FIG. 1 or other methods. The system 10 includes a transmit beamformer 12, a transducer 14, a receive beamformer 16, an image processor 18, a display 20, and a memory 22. Additional, different or fewer components may be provided. For example, a user input is provided for user interaction with the system.

The system 10 is a medical diagnostic ultrasound imaging system. In alternative embodiments, the system 10 is a personal computer, workstation, PACS station, or other arrangement at a same location or distributed over a network for real-time or post acquisition imaging.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated waveforms, one or more beams are formed. A sequence of transmit beams are generated to scan a two or three-dimensional region. Sector, Vector®, linear, or other scan formats may be used. The same region is scanned multiple times. For flow or Doppler imaging and for shear imaging, a sequence of scans is used. In Doppler imaging, the sequence may include multiple beams along a same scan line before scanning an adjacent scan line. For shear imaging, scan or frame interleaving may be used (i.e., scan the entire region before scanning again). In alternative embodiments, the transmit beamformer 12 generates a plane wave or diverging wave for more rapid scanning.

The same transmit beamformer 12 generates impulse excitations or electrical waveforms for generating acoustic energy to cause displacement. In alternative embodiments, a different transmit beamformer is provided for generating the impulse excitation. The transmit beamformer 12 causes the transducer 14 to generate high intensity focused ultrasound waveforms.

The transducer 14 is an array for generating acoustic energy from electrical waveforms. For an array, relative delays focus the acoustic energy. A given transmit event corresponds to transmission of acoustic energy by different elements at a substantially same time given the delays. The transmit event provides a pulse of ultrasound energy for displacing the tissue. The pulse is an impulse excitation. Impulse excitation includes waveforms with many cycles (e.g., 500 cycles) but that occurs in a relatively short time to cause tissue displacement over a longer time.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer 14. The elements connect with channels of the transmit and receive beamformers 12, 16. Alternatively, a single element with a mechanical focus is used.

The receive beamformer 16 includes a plurality of channels with amplifiers, delays, and/or phase rotators, and one or more summers. Each channel connects with one or more transducer elements. The receive beamformer 16 is configured by hardware or software to apply relative delays, phases, and/or apodization to form one or more receive beams in response to each imaging transmission. Receive operation may not occur for echoes from the impulse excitation used to displace tissue. The receive beamformer 16 outputs data representing spatial locations using the receive signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or other band.

In coordination with the transmit beamformer 12, the receive beamformer 16 generates data representing the region at different times. After the acoustic impulse excitation, the receive beamformer 16 generates beams representing different lines or locations at different times. By scanning the region of interest with ultrasound, data (e.g., beamformed samples) is generated.

The receive beamformer 16 outputs beam summed data representing spatial locations. Data for a single location, locations along a line, locations for an area, or locations for a volume are output. Dynamic focusing may be provided. The data may be for different purposes. For example, different scans are performed for B-mode or tissue data than for displacement. Alternatively, the B-mode data is also used to determine displacement. As another example, data for displacement-based classification and shear imaging is performed with a series of shared scans and B-mode or Doppler scanning is performed separately or using some of the same data.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for detecting and processing information for display from beamformed ultrasound samples. In one embodiment, the processor 18 includes one or more detectors and a separate processor. The separate processor is a control processor, general processor, digital signal processor, application specific integrated circuit, field programmable gate array, network, server, group of processors, data path, combinations thereof or other now known or later developed device for determining displacement and calculating displacement profile properties. For example, the separate processor is configured by hardware and/or software to perform any combination of one or more of the acts shown in FIG. 1.

The processor 18 is configured to estimate tissue displacement induced by the acoustic impulse excitation. Using correlation, tracking, motion detection, or other displacement measuring, the amount of shift in position of the tissue is estimated. The estimation is performed multiple times through a period, such as from prior to the tissue moving due to the impulse to after the tissue has mostly or completely returned to a relaxed state (e.g., recovered from the stress caused by the impulse excitation).

The processor 18 is configured to derive at least one parameter describing a characteristic of a profile of the tissue displacement. For example, the signal-to-noise ratio of the displacement profile is derived. As another example, the maximum displacement of the displacement profile is derived. The processor 18 may calculate other parameters, such as a statistic of the data in time, space, or time and space. For example, an average B-mode or acoustic impedance value over time and/or space for each location is calculated.

The processor 18 is configured to classify tissue in the region. Tissue may be fluid tissue or solid tissue. The classification may be between types of tissue, between tissue and fluid, or between types of tissue and one or more other classes. In one embodiment, the processor 18 classifies the material at a location as fluid/fluid tissue, solid tissue, and other/non-determinative.

The classification is based on at least one parameter. For example, the classification is based on values for one or more characteristics of the displacement profile. The signal-to-noise ratio and the maximum displacement are two such characteristics. Other information, such as a statistic of other data, may be used in the classification.

The processor 18 implements fuzzy logic, a probability function, lookup table, or other process. The input features (e.g., characteristics of the displacement profile) are applied to the process to determine a category to which the location should be labeled.

The processor 18 operates pursuant to instructions stored in the memory 22 or another memory for classification preprocessing in medical ultrasound shear wave imaging. The processor 18 is programmed for providing feedback for high intensity focused ultrasound. The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying two-dimensional images or three-dimensional representations. The display 20 is configured by the processor 18 or other device by input of the signals to be displayed as an image. The display 20 displays an image representing shear for different locations in a region of interest or an entire image. The classification is used to segment the locations. Locations associated with solid tissue are modulated or include information for shear. Other locations are masked to not include shear information. The other locations may instead be subject to greater filtering of the shear information.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for classification preprocessing to be used in medical ultrasound shear wave imaging, the method comprising:
    measuring, with an ultrasound system, values of displacement of tissue over time at a first location within a patient in response to an impulse excitation;
    determining, with a processor of the ultrasound system, a maximum of the values of the displacement over time;
    determining, with the processor of the ultrasound system, a signal-to-noise ratio of the values of the displacement over time where the values of the displacement over time are the signal in the signal-to-noise ratio;
    classifying, with the processor, the first location as a first one of a plurality types of tissue where the classifying distinguishes the types of tissue based on a level of fluid in the tissue, the tissue being fluid tissue or solid tissue and being other than bone, the classifying using the maximum of the displacement of the values over time and the signal-to-noise ratio of the values of the displacement over time as variables in the classifying, a SNR level of the signal-to-noise ratio of the values of the displacement over time being an input in the classifying; and
    imaging as a function of the classifying of the first location.

2. The method of claim 1 further comprising:
    transmitting an acoustic excitation into a patient, the impulse excitation comprising the acoustic excitation;
    wherein measuring the values of the displacement comprises repetitively scanning the first location with the ultrasound.

3. The method of claim 1 wherein measuring the values of the displacement comprises transmitting ultrasound to the tissue and receiving reflections from the transmitting, the transmitting the ultrasound and receiving being performed multiple times, and detecting the values of the displacement from the reflections from the multiple receiving.

4. The method of claim 1 further comprising:
    repeating the classifying for a plurality of locations;
    performing shear wave imaging of the patient including the first location and the plurality of locations; and
    spatially masking the shear wave imaging as a function of the classifying for the first location and the plurality of locations.

5. The method of claim 1 wherein measuring the values of the displacement over time comprises measuring the values of the displacement as the tissue relaxes after the impulse excitation.

6. The method of claim 1 wherein determining the signal-to-noise ratio comprises:
    filtering the values of the displacement over time;
    subtracting the filtered values of the displacement over time from the values of the displacement over time;
    calculating a root mean square of a result of the subtracting; and
    dividing an integral of the filtered values of the displacement by the root mean square, a result of the dividing comprising the signal-to-noise ratio.

7. The method of claim 1 wherein classifying comprises classifying the first one as one of a group consisting of the fluid tissue, the solid tissue, and not determinable.

8. The method of claim 1 wherein classifying comprises classifying the first one as the fluid tissue or the solid tissue.

9. The method of claim 1 wherein classifying comprises classifying with fuzzy logic or a probability function.

10. The method of claim 1 further comprising
    determining a signal-to-noise ratio of an ultrasound signal; and
    determining a de-correlation coefficient of the ultrasound signal over time;
    wherein classifying comprises classifying as a function of the maximum of the values of the displacement over time, the signal-to-noise ratio of the values of the displacement over time, the signal-to-noise ratio of the ultrasound signal, and the de-correlation coefficient of the ultrasound signal over time.

11. In a non-transitory computer readable storage medium having stored therein data representing instructions executable by a programmed processor for classification preprocessing in medical ultrasound shear wave imaging, the storage medium comprising instructions for:
    determining, with an ultrasound system, a displacement profile of response in a patient, the displacement profile being a curve of displacements for a location over a plurality of times;
    calculating, by the processor, a first characteristic of just the displacement profile;
    distinguishing fluid and cyst tissue from solid tissue based, at least in part, on the first characteristic, the cyst tissue and solid tissue being other than bone;
    displaying an image of shear wave information; and
    masking out, in the image and by the processor, shear wave information from the fluid or fluid tissue so that the shear wave information determined for the fluid or cyst tissue locations is not shown in the image.

12. The non-transitory computer readable storage medium of claim 11 wherein determining the displacement profile comprises receiving data representing a region of the patient at different times and correlating the data.

13. The non-transitory computer readable storage medium of claim 11 wherein determining the displacement profile comprise determining a magnitude of displacement as a function of time after an impulse causing displacement of tissue in the patient.

14. The non-transitory computer readable storage medium of claim 11 wherein calculating comprises calculating a signal-to-noise ratio of the displacement profile.

15. The non-transitory computer readable storage medium of claim 11 wherein calculating comprises calculating a maximum displacement from the displacement profile.

16. The non-transitory computer readable storage medium of claim 11 wherein distinguishing comprises classifying as a function of the first characteristic.

17. The non-transitory computer readable storage medium of claim 11 wherein distinguishing comprises classifying between (a) the fluid and the cyst tissue, (b) solid tissue, and (c) another class.

18. The non-transitory computer readable storage medium of claim 11 wherein masking comprises displaying the image representing shear wave information for solid tissue regions and not for fluid or cyst tissue regions.

19. A system for classification preprocessing in medical ultrasound shear wave imaging, the system comprising:
- a transducer configured to transmit an acoustic impulse excitation into a patient and configured to scan with ultrasound a region of the patient;
- a receive beamformer configured to generate data representing the region at different times after the acoustic impulse excitation, the data generated from the scan with ultrasound;
- a processor configured to estimate tissue displacement induced by the acoustic impulse excitation, derive at least one parameter describing a characteristic of a profile curve of the tissue displacement over time, and classify tissue in the region based on at least the one parameter, the classification of tissue being of a level of fluid in the tissue where the tissue is other than bone or fluid; and
- a display configured to display an image representing shear for first locations and no shear information for second locations, the first and second locations determined from the classification of the tissue.

20. The system of claim 19 wherein the processor is configured to derive the one parameter as a signal-to-noise ratio, is configured to derive another parameter as a maximum displacement of the profile, and is configured to classify based on the signal-to-noise ratio and the maximum displacement.

21. The system of claim 19 wherein the processor is configured to derive the one parameter as a signal-to-noise ratio, is configured to derive another parameter as a maximum displacement of the profile, is configured to compute a statistic of the data in time, space, or time and space, and is configured to classify based on the statistic, signal-to-noise ratio and the maximum displacement.

22. The non-transitory computer readable storage medium of claim 11 wherein distinguishing comprises distinguishing for each of a plurality of locations between different classes representing a class for more reliable shear measurement and a class for less reliable shear measurement.

* * * * *